(12) United States Patent
Kunikata et al.

(10) Patent No.: US 10,690,624 B2
(45) Date of Patent: Jun. 23, 2020

(54) ELECTROCHEMICAL MEASUREMENT METHOD, ELECTROCHEMICAL MEASUREMENT DEVICE AND TRANSDUCER

(71) Applicants: JAPAN AVIATION ELECTRONICS INDUSTRY, LIMITED, Tokyo (JP); TOHOKU UNIVERSITY, Miyagi (JP)

(72) Inventors: Ryota Kunikata, Tokyo (JP); Hiroyuki Hayashi, Tokyo (JP); Atsushi Suda, Tokyo (JP); Kosuke Ino, Miyagi (JP); Kumi Inoue, Miyagi (JP); Tomokazu Matsue, Miyagi (JP)

(73) Assignees: JAPAN AVIATION ELECTRONICS INDUSTRY, LIMITED, Tokyo (JP); TOHOKU UNIVERSITY, Miyagi (JP)

( * ) Notice: Subject to any disclaimer, the term of this patent is extended or adjusted under 35 U.S.C. 154(b) by 20 days.

(21) Appl. No.: 16/063,570

(22) PCT Filed: Nov. 2, 2016

(86) PCT No.: PCT/JP2016/082638
§ 371 (c)(1),
(2) Date: Jun. 18, 2018

(87) PCT Pub. No.: WO2017/110258
PCT Pub. Date: Jun. 29, 2017

(65) Prior Publication Data
US 2018/0372676 A1   Dec. 27, 2018

(30) Foreign Application Priority Data

Dec. 22, 2015 (JP) ................................. 2015-249764
Mar. 18, 2016 (JP) ................................. 2016-055283

(51) Int. Cl.
*C12M 1/34* (2006.01)
*G01N 27/327* (2006.01)
(Continued)

(52) U.S. Cl.
CPC ............. *G01N 27/416* (2013.01); *C12M 1/34* (2013.01); *C12M 41/30* (2013.01); *C12Q 1/00* (2013.01);
(Continued)

(58) Field of Classification Search
CPC ...... C12M 41/28; C12M 41/30; C12M 41/46; G01N 27/327
See application file for complete search history.

(56) References Cited

U.S. PATENT DOCUMENTS

| | | |
|---|---|---|
| 2009/0297913 A1 | 12/2009 | Zhang et al. |
| 2015/0260675 A1 | 9/2015 | Nakatani et al. |
| 2017/0336384 A1 | 11/2017 | Ino et al. |

FOREIGN PATENT DOCUMENTS

| | | |
|---|---|---|
| EP | 1406086 A1 | 4/2004 |
| JP | 2005-148058 A | 6/2005 |

(Continued)

OTHER PUBLICATIONS

Office Action issued in Singapore family member Patent Appl. No. 11201804875R, dated Mar. 20, 2019.
(Continued)

*Primary Examiner* — Alexander S Noguerola
(74) *Attorney, Agent, or Firm* — Greenblum & Bernstein, P.L.C.

(57) ABSTRACT

An electrochemical measurement method for electrochemically measuring a chemical substance generated or consumed in a biological sample in a solution is provided which includes performing measurement by placing the biological sample at a distance away from an electrode surface in the direction perpendicular to the electrode surface. The distance is determined in advance on the basis of simulation in which a current flows through a working electrode.

15 Claims, 6 Drawing Sheets

(51) Int. Cl.
  *G01N 27/416* (2006.01)
  *C12Q 1/00* (2006.01)
  *G01N 33/50* (2006.01)
  *C12Q 1/42* (2006.01)
  *G01N 33/487* (2006.01)

(52) U.S. Cl.
  CPC .............. *C12Q 1/42* (2013.01); *G01N 27/327* (2013.01); *G01N 33/48707* (2013.01); *G01N 33/5082* (2013.01)

(56) References Cited

FOREIGN PATENT DOCUMENTS

| WO | 2010/025547 | A1 | 3/2010 |
| WO | 2014/073195 | A1 | 5/2014 |
| WO | 2015/151395 | A1 | 10/2015 |

OTHER PUBLICATIONS

Kanno et al., "Simulation analysis of positional relationship between embryoid bodies and sensors on an LSI-based amperometric device for electrochemical imaging of alkaline phosphatase activity", Analytical Sciences, Jul. 10, 2015, pp. 715-719.

Sen et al., "LSI-based amperometric sensor for real-time monitoring of embryoid bodies", Biosensors and Bioelectronics, 2013, pp. 12-18.

Ino et al., "Electrochemical device with interdigitated ring array electrodes for investigating the relationship between cardiomyocyte differentiation from embryonic stem cells and alkaline phosphatase activity", Electrochemistry, 2013, pp. 682-687.

U.S. Appl. No. 15/776,195 to Hiroyuki Hayashi et al., filed May 15, 2018.

Office Action issued in European Patent Office (EPO) family member Patent Appl. No. 16878156.5, dated Oct. 17, 2018.

Chinese Office Action for CN Application No. 201680074909.9, dated Oct. 21, 2019, and English-language translation thereof.

ELECTROCHEMICAL MEASUREMENT METHOD, ELECTROCHEMICAL MEASUREMENT DEVICE AND TRANSDUCER

TECHNICAL FIELD

The present invention relates to an electrochemical measurement method, an electrochemical measurement device and a transducer used in electrochemical measurement for electrochemically measuring a chemical substance generated or consumed in cells, cell aggregates, pieces of tissue and other biological samples, and non-biological samples containing biologically-relevant substances (which are collectively simply referred to as "biological samples" hereafter).

BACKGROUND ART

Developing techniques for quantitatively evaluating chemical substances generated or consumed in cells significantly contributes not only to development of fundamental biochemistry but also to the medical and life science fields, such as cytoscreening used for cancer screening tests and the like, quality evaluation of transplantation cells used in regenerative medicine, immune cell therapies and the like, and for use as substitutes for experimentation on animals for drug efficacy assessments and toxicity assessments.

However, bioactivities of cells vary with environments surrounding the cells, such as temperature, pH, medium compositions, adjacent cells, and extracellular matrixes and also vary over time depending on external stimuli such as gene introduction, drug exposure, application of stress and the like and cell events such as cell division and cell death.

Therefore, in order to evaluate true properties of cells that actually act in a biological body, it is important to place sample cells alive (while maintaining cell bioactivities) in an environment that is as close to an intravital environment as possible and to measure a chemical substance generated or consumed in the cells in real-time with respect to external stimuli and cell events.

One widely-used method for placing sample cells in an environment that is close to an intravital environment is to select as a sample a cell aggregate (spheroid) which is an aggregate of multiple cells and extracellular matrix (ECM) components, rather than a single cell.

This is because many of various bioactivities of cells undergo interaction with adjacent cells and ECM that contact the cells and therefore a cell aggregate which is an aggregate of them may replicate an intravital environment more faithfully.

Such cell aggregates may include spheroids of pancreatic islet cells obtained from pancreas, fertilized eggs, liver cells and nerve cells obtained through cell culture and embryoid bodies of embryonic stem (ES) cells.

While such cell aggregates have diameters that differ depending on the types of component cells, regions in a biological body from which the cell aggregates were obtained, culture conditions and the like, cell aggregates having diameters of about 100 to 600 µm are often used in evaluation of cell activities. This is because the number of component cells in a small cell aggregate with a diameter of 100 µm or smaller is too small for bioactivities specific to cell aggregates to appear whereas in a large cell aggregate having a diameter of 600 µm or greater, oxygen does not diffuse to cells in the central part of the cell aggregate and cell necrosis is likely to occur.

As an approach to measuring a chemical substance generated or consumed in cells in real-time, an electrochemical approach is used. The electrochemical approach requires electrodes (working electrodes) that are placed in the same solution together with a sample and used for detecting various electrochemical signals from the sample. There are various detection methods with variations in potential control or current control of the working electrodes. In measurement relating to metabolic activities of cells or the like, potentiostatic electrolysis (constant-potential electrolysis) exemplified by chronoamperometry and cyclic voltammetry have been used because of its high comparison performance and simplicity of analysis. In the potentiostatic electrolysis, the potential of a working electrode is controlled as a function of time and a current value that appears in the working electrode is detected during the control.

In electrochemical measurement of a chemical substance generated or consumed in a common cell aggregate, a reaction system that causes a chemical substance having a redox activity to be generated inside the cell aggregate or at the surface of the cell aggregate in association with substance metabolism of the cell aggregate is incorporated and is oxidized or reduced on a working electrode to generate a current.

While various systems can be designed that depend on a metabolic system of interest as reaction systems that cause a chemical substance having a redox activity to be generated in association with substance metabolism of cells, systems that use an enzyme reaction are popularly used among others for the purpose of detecting a trace amount of metabolic substance with high sensitivity.

For example, in an embryoid body which is a cell aggregate made from mouse ES cells, the amount of alkaline phosphatase (ALP) which is an enzyme existing at the surface of cells increases or decreases depending on the differentiation state of the embryoid body.

In order to evaluate the differentiation state of an embryoid body, electrochemical evaluation of the amount of generated ALP is often performed (Non-patent literature 1). In the evaluation system, an embryoid body is placed in a solution in which p-aminophenyl phosphate (PAPP), which is a substrate substance, is dissolved and a dephosphorylation is facilitated by ALP enzyme activity, thereby generating p-aminophenol (PAP) having redox activity.

When the PAPP concentration in the solution is sufficiently high, the amounts of PAP, which is a redox-active chemical substance, can be accumulated with time by the enzymic activity of PAP even though the amount of ALP generated from cells is ultralow. Consequently, the amount of existing ALP can be detected with high sensitivity.

PRIOR ART LITERATURE

Non-Patent Literature

Non-patent literature 1: M. Sen, et al., "Biosensors and Bioelectronics", 2013, Vol. 48, pp. 12-18

SUMMARY OF THE INVENTION

Problems to be Solved by the Invention

A redox-active chemical substance that is generated or consumed in cells radially spread by diffusion mechanism with the cells being placed at a center unless an external special hydrodynamic action is exerted and part of the chemical substance reaches a working electrode and undergoes oxidization or reduction. Accordingly, the amount of current generated at this point of time is significantly affected by the amount of the chemical substance generated or consumed and the distance of diffusion of the chemical substance to the working electrode.

However, if a working electrode is formed on a substrate and a sample is positioned close to the working electrode, supply of a substrate substance dissolved in a solution to the sample is inhibited because of the small spacing between the sample and the substrate. Consequently, the amount of a chemical substance generated from the sample by an enzyme reaction is smaller than when a sample is away from the substrate and suspended in the solution. In addition, since the volume of space between the sample and the working electrode is small, most of the chemical substance generated cannot remain in the space and scatters away. Since the scattered chemical substance is at a longer distance to the working electrode, the amount of the chemical substance that reaches the working electrode decreases and, as a result, the sensitivity decreases (problem 1).

Further, since there is an influence of unevenness of the surface of a sample and the sample is not necessarily spherical, the precision of control of the vertical distance between the working electrode and the ample is limited. Since the vertical distance can vary typically at least by several micrometers each time measurement is performed, the diffusion distance of a chemical substance becomes inconstant and the comparison performance and reproducibility of measurement decrease (problem 2).

In Non-patent literature 1, the amounts of chemical substances are measured using working electrodes on a substrate, which has problems 1 and 2 described above.

On the other hand, probe-like working electrodes (probe electrodes) are sometimes used instead of working electrodes on a substrate. Since the tip of a probe electrode is typically much smaller than a sample, the inhibition of supply of a dissolved substance to the sample in a solution by the probe electrode and its support is smaller than the inhibition by an electrode on a substrate. Accordingly, problem 1 described above is not significant. Further, the position of a probe electrode with respect to a sample is usually controlled finely on the order of micrometers by a manipulator. Accordingly, problem 2 described above does not arise.

However, control of the position of a probe electrode requires expensive equipment such as a manipulator and microscope system for observing the position of the probe tip. In addition, probe electrodes are often broken by inexperienced users.

An object of the present invention is to provide an electrochemical measurement method, an electrochemical measurement device and a transducer used in electrochemical measurement that are capable of improving sensitivity, comparison performance and reproducibility of electrochemical measurement that uses working electrodes formed on a substrate, for example, and placed and fixed in a solution rather than using probe electrodes as working electrodes.

Means to Solve the Problems

An electrochemical measurement method according to a first aspect of the present invention is an electrochemical measurement method for electrochemically measuring a chemical substance generated or consumed in a biological sample in a solution, which includes: performing a simulation in which given condition includes a dimension of an electrode surface of a working electrode that supplies and receives electrons to and from the chemical substance to cause an oxidation-reduction reaction and a dimension of the biological sample and a current flowing through the working electrode is calculated on the basis of a rate of a chemical reaction in which the chemical substance is generated or consumed in the biological sample, a change in a concentration distribution of the chemical substance in the solution, and rate at which electrons are supplied and received to and from the chemical substance at the electrode surface, the simulation being performed by using, as a variable, a distance between the biological sample and the electrode surface in the direction perpendicular to the electrode surface to obtain a range of the distance in the vertical direction that includes a point at which the current takes a maximum value and within which the current value is greater than or equal to 90% of the maximum value; and performing measurement by placing the biological sample in the solution at a distance away from the electrode surface in the direction perpendicular to the electrode surface, the distance falling within the range.

An electrochemical measurement method according to a second aspect of the present invention is an electrochemical measurement method for electrochemically measuring a chemical substance generated or consumed in a biological sample in a solution that has a diameter dimension between 100 µm, inclusive, and 600 µm, inclusive, by using a working electrode that has a diameter dimension $d_{el}$ less than or equal to 80 µm and supplies and receives electrons to and from the chemical substance to cause an oxidation-reduction reaction, wherein a spacer is placed in the solution, the spacer having a profile surface at a distance $h_1$ in the direction perpendicular to the electrode surface, the distance $h_1$ satisfying $$h_1 = 21.8 \frac{d_{el} + 0.8}{d_{el} + 9.7} \pm 5 \ [\mu m] \qquad \text{[Formula 1]}$$

the spacer preventing the biological sample from entering a region on the electrode surface side of the profile surface and allowing a dissolved substance to diffuse in the solution; and measurement is performed while the biological sample is positioned along the profile surface of the spacer.

An electrochemical measurement method according to a third aspect of the present invention is an electrochemical measurement method for electrochemically measuring a chemical substance generated or consumed in a biological sample in a solution that has a diameter dimension between 100 µm, inclusive, and 600 µm, inclusive, by using a working electrode that has a diameter dimension $d_{el}$ less than or equal to 80 µm and supplies and receives electrons to and from the chemical substance to cause an oxidation-reduction reaction, wherein a spacer is placed in the solution, the spacer having an inverse-cone-shaped profile surface at a distance $h_2$ in the direction perpendicular to the electrode surface, the distance $h_2$ being dependent on a distance m from a center of the electrode surface in the direction parallel to the electrode surface and satisfying $$h_2 = \sqrt{\{(1.05 d_{el} + 6.89)m\} - 0.48 d_{el} - 2.38} \pm 5 [\mu m]$$

the spacer preventing the biological sample from entering a region on the electrode surface side of the profile surface and allowing a dissolved substance in the solution to diffuse; and measurement is performed while the biological sample is positioned immediately above the center of the electrode surface along the profile surface of the spacer.

An electrochemical measurement device according to the second aspect of the present invention is an electrochemical measurement device for electrochemically measuring a chemical substance generated or consumed in a biological sample in a solution by using a working electrode that includes an electrode surface supplying and receiving electrons to and from the chemical substance to cause an oxidation-reduction reaction, wherein the electrode surface has a diameter dimension $d_{el}$ less than or equal to 80 μm; and a spacer is provided in a solution well containing the solution and the biological sample, the spacer having a profile surface at a distance $h_1$ in the direction perpendicular to the electrode surface, the distance $h_1$ satisfying $$h_1 = 21.8 \frac{d_{el} + 0.8}{d_{el} + 9.7} \pm 5 \ [\mu m] \quad \text{[Formula 2]}$$

the spacer preventing the biological sample from entering a region on the electrode surface side of the profile surface and allowing a dissolved substance to diffuse in the solution.

An electrochemical measurement device according to the third aspect of the present invention is an electrochemical measurement device for electrochemically measuring a chemical substance generated or consumed in a biological sample in a solution by using a working electrode that includes an electrode surface supplying and receiving electrons to and from the chemical substance to cause an oxidation-reduction reaction, wherein the electrode surface has a diameter dimension $d_{el}$ less than or equal to 80 μm; and a spacer is provided in a solution well containing the solution and the biological sample, the spacer having an inverse-cone-shaped profile surface at a distance $h_2$ in the direction perpendicular to the electrode surface, the distance $h_2$ being dependent on a distance m from a center of the electrode surface in the direction parallel to the electrode surface and satisfying $$h_2 = \sqrt{\{(1.05d_{el} + 6.89)m\}} - 0.48d_{el} - 2.38 \pm 5 [\mu m]$$

the spacer preventing the biological sample from entering a region on the electrode surface side of the profile surface and allowing a dissolved substance to diffuse in the solution.

A transducer according to the second aspect of the present invention is a transducer including a solution well that can contain a solution and a biological sample immersed in the solution, the solution well being mounted on an LSI chip, the transducer being used for electrochemical measurement of a chemical substance generated or consumed in the biological sample, wherein an electrode provided on the LSI chip, positioned at a bottom surface of the solution well and having an electrode surface with a diameter dimension $d_{el}$ less than 80 μm, and a spacer fabricated above the electrode and having a profile surface at a distance $h_1$ in the direction perpendicular to the electrode surface, the distance $h_1$ satisfying $$h_1 = 21.8 \frac{d_{el} + 0.8}{d_{el} + 9.7} \pm 5 \ [\mu m] \quad \text{[Formula 3]}$$

the spacer preventing the biological sample from entering a region on the electrode surface side of the profile surface and allowing a dissolved substance to diffuse in the solution, are provided in the solution well.

A transducer according to the third aspect of the present invention is a transducer including a solution well that can contain a solution and a biological sample immersed in the solution, the solution well being mounted on an LSI chip, the transducer being used for electrochemical measurement of a chemical substance generated or consumed in the biological sample, wherein an electrode provided on the LSI chip, positioned at a bottom surface of the solution well and having an electrode surface with a diameter dimension $d_{el}$ less than 80 μm, and a spacer fabricated above the electrode and having an inverse-cone-shaped profile surface at a distance $h_2$ in the direction perpendicular to the electrode surface, the distance $h_2$ being dependent on a distance m from a center of the electrode surface in the direction parallel to the electrode surface, the distance $h_2$ satisfying $$h_2 = \sqrt{\{(1.05d_{el} + 6.89)m\}} - 0.48d_{el} - 2.38 \pm 5 [\mu m]$$

the spacer preventing the biological sample from entering a region on the electrode surface side of the profile surface and allowing a dissolved substance to diffuse in the solution, are provided in the solution well.

Effects of the Invention

In an electrochemical measurement method according to the present invention, measurement is performed with a biological sample being positioned at a predetermined distance away from the electrode surface of a working electrode in the direction perpendicular to the electrode surface, thereby providing a space through which a dissolved substance in a solution can diffuse to supply a sufficient amount of the dissolved substance to the biological sample.

The electrochemical measurement method according to the present invention is therefore capable of increasing the amount of a chemical substance generated or consumed in the biological sample and detected at the working electrode and improving the sensitivity of measurement accordingly as compared with conventional electrochemical measurement methods in which measurement is performed with a biological sample being positioned close to the electrode surface of a working electrode.

In addition, since the biological sample is positioned at a predetermined distance away from the electrode surface of the working electrode, the measurement method of the present invention is capable of reducing influences of variations in the distance of diffusion of the chemical substance that are associated with variations in the vertical distance between the working electrode and the biological sample due to the shape and surface conditions of the biological sample, thereby improving the comparison performance and reproducibility of measurement as compared with conventional electrochemical measurement methods in which a biological sample is positioned close to the electrode surface of a working electrode.

Further, an electrochemical measurement device and a transducer according to the present invention enable such electrochemical measurement to be successfully performed.

DETAILED DESCRIPTION OF THE EMBODIMENTS

Figure 1:
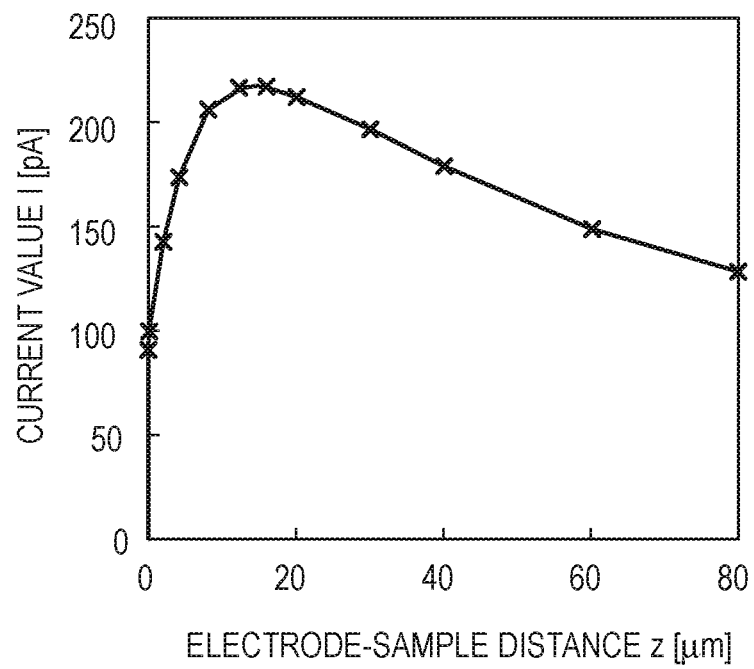
FIG. 1 is a graph illustrating the relationship between electrode-sample distance z and current value I.

Relationship between a process of diffusion of a dissolved substance in a solution relating to a chemical reaction occurring in a sample and a current flowing through an electrode on a substrate was analyzed in detail in electrochemical measurement and it was found that the amount of current was increased and the sensitivity of measurement was improved by positioning a sample at a certain distance determined by the electrode diameter and the sample diameter away from the electrode in the direction perpendicular to the electrode surface to form, below the sample, a path through which the solution freely diffuse, as compared with when the sample is positioned immediately above and close to the electrode.

Further, it was found that variations in current values caused by low precision of position control of a sample with respect to the electrode was decreased by positioning the sample away from the electrode in the direction perpendicular to the electrode surface and the comparison performance and reproducibility of measurement were improved as compared with variations when the sample was positioned immediately above and close to the electrode.

First, the results of a simulation that have led to the findings described above will be described below.

Simulation software COMSOL Multiphysics was used in the simulation. An embryoid body formed from mouse ES cells was chosen as a model sample. As a chemical substance to be generated from the sample, PAP generated by ALP enzyme reaction at the surface of the sample was chosen. It was assumed that the chemical substance generated from the sample diffuses to an electrode (working electrode), then causes oxidation-reduction reaction on the electrode and is detected as current values. The other conditions were as given below.

<Enzyme Reaction>

ALP enzyme reaction using PAPP which is a dissolved substance in a solution progresses and PAP is generated. The rate of the reaction (generation speed) v was assumed to follow the Michaelis-Menten equation (1) given below.

[Formula 4]

$$v = \frac{A_{sp} V_{max} [S]}{K_m + [S]} \quad (1)$$

Here, $A_{sp}$ is the surface area of the sample, $V_{max}$ is the reaction rate per unit surface area of the sample when the substrate substance concentration is infinite, $K_m$ is the Michaelis constant of ALP enzyme reaction, and [S] is the substrate substance concentration. Values of $V_{max}$ and $K_m$ were set at $2.65 \times 10^{-7}$ mol/(s·m²) and $1.7 \times 10^{-3}$ mol/L, respectively. The initial value of [S] was $5.0 \times 10^{-3}$ mol/L.

<Electrode Reaction>

It was assumed that double-electron oxidation reaction of PAP generated from the sample progresses on the electrode. Electrode potential was assumed to be sufficiently high for the reaction to be a complete diffusion-controlled reaction. The current value I during the reaction was assumed to follow the equations (2) and (3) given below.

[Formula 5]

$$I = \int_{A_{el}} i(x, y) dA_{el} \quad (2)$$

$$i(x, y) = nFD \frac{dc(x, y)}{dz} \quad (3)$$

Here, i(x, y) and c(x, y) are the current density and the concentration of the chemical substance to be detected, respectively, at an arbitrary point (x, y) on the electrode surface, $A_{el}$ is the area of the electrode, n is the number of electrons involved in the reaction, F is the Faraday constant, and D is the diffusion coefficient of the chemical substance to be detected in the solution. n, F, and D were set at 2, $9.64 \times 10^4$ C/mol, and $6.47 \times 10^{-10}$ m²/s, respectively. The current value I acquired 200 seconds after the start of electrode reaction was shown as a measurement calculation result.

<Other Conditions>

Sample shape: Diameter $d_{sp}$=200 µm, spherical

Electrode (electrode surface) shape: diameter $d_{el}$=20 µm, circular

Electrode position: Set such that the horizontal distance between the electrode surface central coordinates and the sample central coordinates (x, y) is 0

Distance z between the electrode surface and the lower end of the sample: 0-80 µm It was investigated how the current value I resulting from oxidation-reduction reaction of the chemical substance generated from the sample changed depending on the distance z between the electrode and the lower end of the sample. FIG. 1 illustrates the result of the simulation indicating the relationship between current value I and distance z.

It can be seen from the result that the plot of the current value I is an arc-shaped curve with the peak at z=16 µm. Thus, it was found that by placing a sample at an optimum distance at which the peak current value can be obtained, the sensitivity of measurement can be significantly improved as compared with when the sample was at a distance z=0 µm. Tendencies of z similar to this tendency of z were obtained when the electrode diameter $d_{el}$ and the sample diameter $d_{sp}$ were changed.

Further, it can be seen that when z is at or near the optimum distance described above, variations in the current value I as z changes up and down are significantly smaller than when z=0 µm. When the sample is a cell, a cell aggregate, a piece of tissue or the like, it is difficult to control z with a precision of several micrometers because there are influences of unevenness of the sample surface and the sample is not necessarily spherical in shape. However, setting z at or near the optimum distance as described above can reduce variations in the current value I due to low controllability of z, resulting in improvements in relative quantitative performance and reproducibility.

Effects of the improvements in relative quantitative performance and reproducibility becomes more remarkable as z is positioned closer to the optimum distance and are especially remarkable when z is in a range in which the current value is 90% or greater of the peak current value. Thus, it can be seen that by setting z at a value in this range, high effects can be achieved in terms of an improvement in sensitivity as well as improvements in relative quantitative performance and reproducibility.

It has been shown from results of various simulations performed that the range of effective z described above significantly varies depending on measurement conditions, in particular the electrode diameter and the sample diameter. Therefore, in order to evaluate a sample that has a particular diameter, an electrode that has an appropriate diameter and appropriate z need to be provided.

However, in the case of biological samples such as cells, cell aggregates or pieces of tissue, the diameters of the samples widely vary depending on the types and conditions of component cells. Further, the diameters of samples taken from the same region of the same test body or samples acquired under the same culture conditions vary from one sample to another by several to several hundred micrometers. Checking the diameter of every such sample and setting an appropriate electrode diameter and z before measurement is unrealistic in terms of cost. Further, it is significantly difficult to quantitatively compare measurement results acquired with different electrode diameters and values of z with one another.

In order to solve these problems, it is effective to determine electrode diameters and ranges of z that can provide high advantageous effects of the present invention for all of samples having various diameters in a reasonable range and to measure various samples by an electrochemical measurement device having the same configuration by using the determined electrode diameters and ranges of z.

Therefore, in the present invention, for cell aggregate samples, which are said to more accurately reproduce bioactivities in biological bodies, electrode diameters and a range of z with which the effect of improving sensitivity, relative quantitative performance and reproducibility can be achieved even when their diameters vary in a commonly used range between 100-600 µm were determined. The procedure will be described below.

Figure 2:
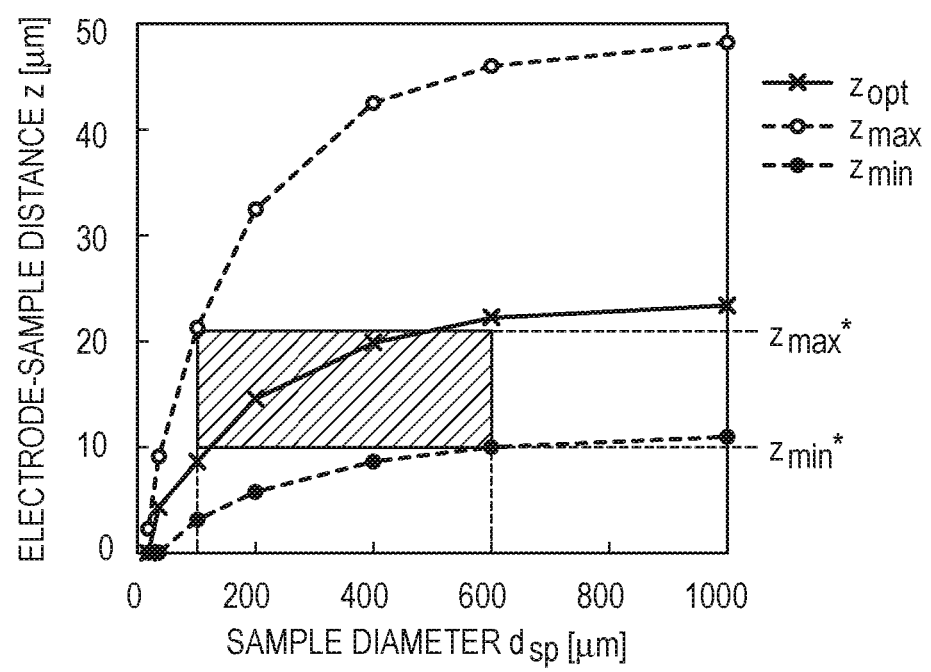
FIG. 2 is a graph illustrating the relationship between sample diameter $d_{sp}$ and effective electrode-sample distance z.

First, it was investigated how the lower limit value $Z_{min}$ and the upper limit value $z_{max}$ of a range of an effective z changes with sample diameters $d_{sp}$ when the electrode diameter $d_{el}$ was 20 µm. FIG. 2 illustrates the result of the simulation. When z is between $z_{min}$, inclusive and $z_{max}$, inclusive, shown in FIG. 2 for each $d_{sp}$ with $d_{el}$ of 20 µm, the effect of the current value I becoming 90% or greater of the peak current value can be provided. ($Z_{opt}$ is the optimum distance z that produces the peak current value.) Also, the effect of the current value I becoming 90% or greater of the peak current value can be provided when z is in the range between the lower limit $z_{min}*$ and the upper limit $z_{max}*$ indicated by the hatching in FIG. 2 with any value of $d_{sp}$ between 100-600 µm, where $z_{max}*$ is $z_{max}$ when $d_{sp}$ is 100 µm and $z_{min}*$ is $z_{min}$ when $d_{sp}$ is 600 µm.

Figure 3:
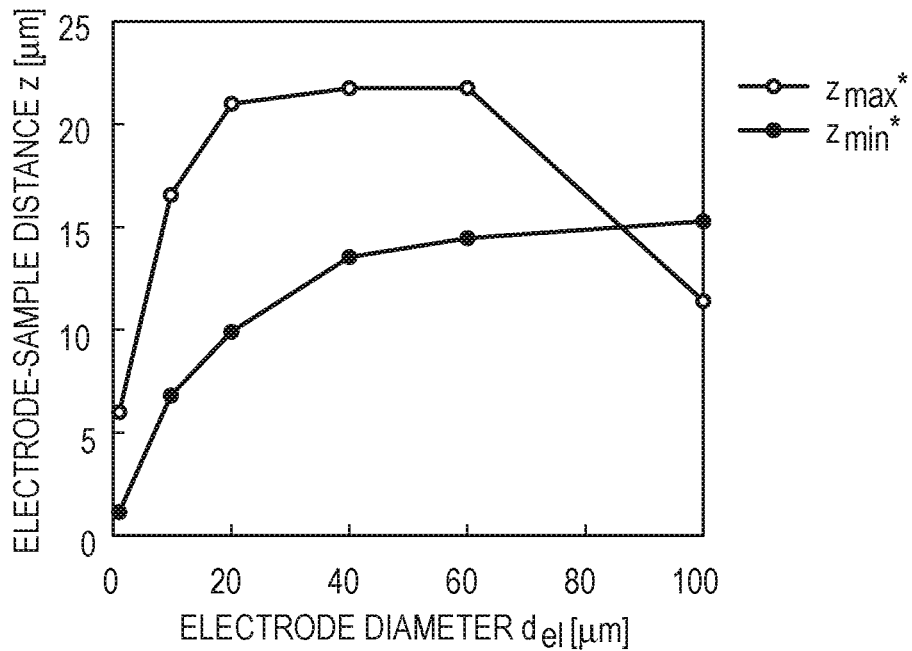
FIG. 3 is a graph illustrating the relationship between electrode diameter $d_{el}$ and effective electrode-sample distance z.

Then, it was investigated how $z_{min}*$ and $z_{max}*$ changes with $d_{el}$. FIG. 3 illustrates the result of the simulation. At any value of $d_{el}$ in the range of 0-80 µm, high advantageous effect of the present invention can be provided for samples with $d_{sp}$=100-600 µm when z is between $z_{min}*$, inclusive, and $z_{max}*$, inclusive, shown in FIG. 3. By fitting operation using the method of nonlinear least square, the range can be roughly expressed as a function of $d_{el}$ by the equation (4) given below.

[Formula 6]

$$z = 21.8 \frac{d_{el} + 0.8}{d_{el} + 9.7} \pm 5 \quad [\mu m] \tag{4}$$

Therefore, z may be set in the range expressed by equation (4), where z>0.

Note that, as can be seen from FIG. 3, equation (4) given above cannot be used when the electrode diameter $d_{el}$ is approximately 80 µm or greater. However, in electrochemical measurement on minute samples such as cells, electrodes with $d_{el}$=50 µm or smaller are commonly used. This is because the S/N ratio of a current value (the ratio between a Faraday current generated by an oxidation-reduction reaction of a chemical substance to be detected and a charging current generated by an electrolyte which is not the substance to be detected) significantly increases at an electrode with $d_{el}$=50 µm or smaller. Therefore, although equation (4) given above cannot be used when the electrode diameter $d_{el}$ is 80 µm or greater, that does not pose a problem.

A range of effective z can vary depending on the generation rate v of a chemical substance from a sample and the diffusion coefficient D of the chemical substance, in addition to electrode diameter $d_{el}$ and sample diameter $d_{sp}$ but their influences are limited.

Figure 4:
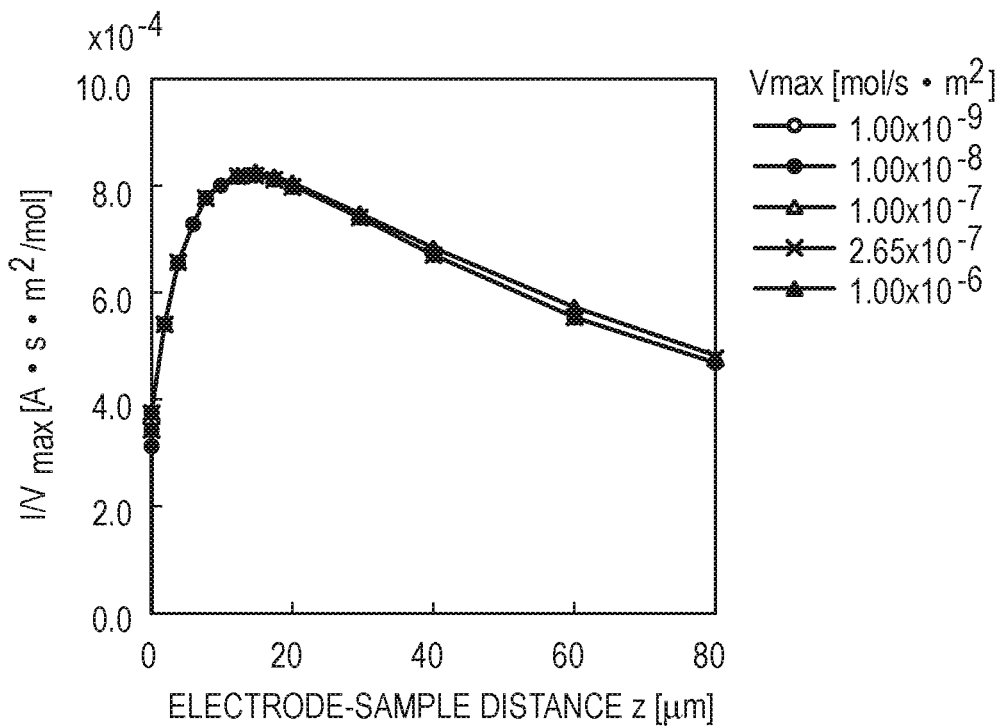
FIG. 4 is a graph illustrating the relationship among electrode-sample distance z, current value I and reaction rate $V_{max}$.

It can be seen from equation (1) that when the substrate substance concentration [S] is sufficiently high, v is virtually determined by the reaction rate $V_{max}$ at infinite substrate substance concentration. Accordingly, it was investigated how the range of effective z changes with $V_{max}$. FIG. 4 illustrates the result of a simulation of current value I at various $V_{max}$ and z. The vertical axis of the graph represents I normalized with $V_{max}$. It can be seen from FIG. 4 that the relationship between I normalized with $V_{max}$ and z remain almost unchanged as $V_{max}$ changes and accordingly the range of effective z is almost unchanged.

Figure 5:
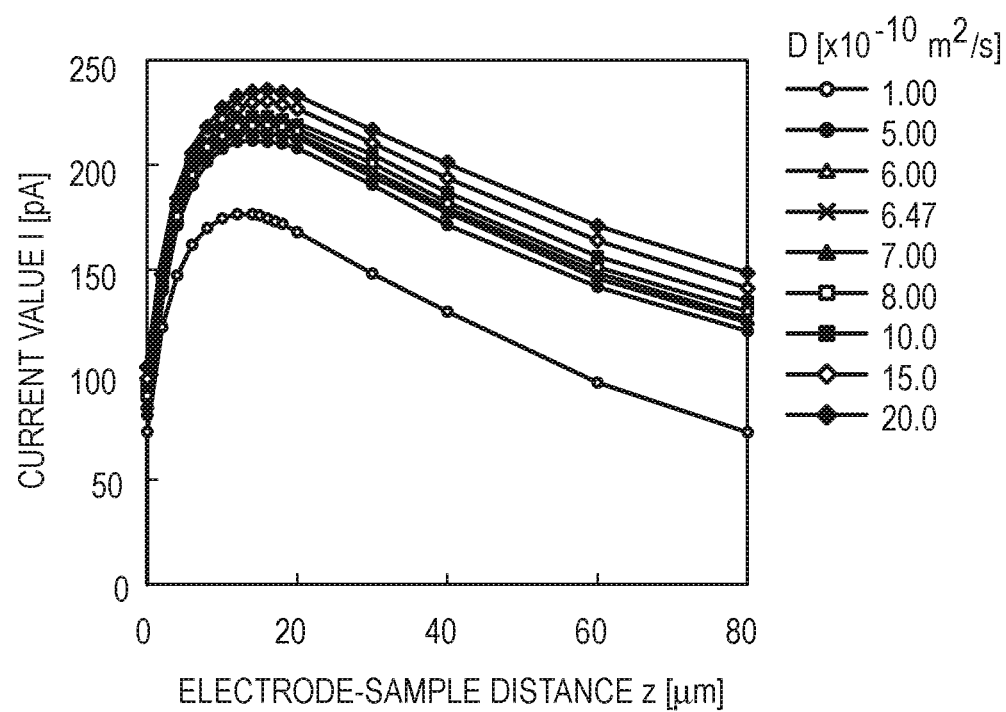
FIG. 5 is a graph illustrating the relationship among electrode-sample distance z, current value I and diffusion coefficient D.

Similarly, it was investigated how the range of effective z changes with D. FIG. 5 illustrates the result of the simulation of I at various D and z. Values of D of typical chemical substances to be detected used in the medical and life science fields, such as PAP, iron complexes, ruthenium complexes, and hydrogen peroxide, are generally in the range of $1$-$20 \times 10^{-10}$ m$^2$/s. It can be seen from FIG. 5 that when D changes in this range, the relationship between I and z remains almost unchanged and therefore the range of effective z is almost unchanged.

It can be seen from the results that equation (4), which represents the relationship between z and $d_{el}$ that needs to be satisfied in order to provide high advantageous effects of the present invention for samples with diameters of 100-600 µm is also useful for measurement systems that have various v and D.

Based on the simulation results described above, according to the present invention, in an electrochemical measurement method for electrochemically measuring a chemical substance generated or consumed in a biological sample having a diameter dimension (diameter) between 100 μm, inclusive, and 600 μm, inclusive in a solution by using a working electrode with an electrode surface having a diameter dimension (diameter) $d_{el}$ less than or equal to 80 μm that supplies and receives electrons to and from the chemical substance to cause oxidation-reduction reaction, a spacer that has a profile surface in which a distance $h_1$ in the direction perpendicular to the electrode surface satisfies the range of z represented by equation (4), prevents the biological sample from entering a region on the electrode surface side of the profile surface and allows a dissolved substance in the solution to diffuse is placed in the solution and the biological sample is positioned along the profile surface of the spacer.

Figure 6:
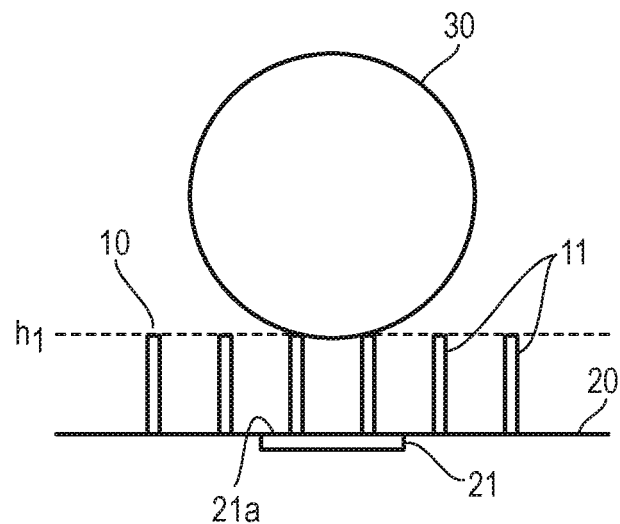
FIG. 6 is a schematic diagram for explaining an example configuration and arrangement of a spacer having uniform height.

FIG. 6 illustrates an example in which spacer 10 is formed by a group of pillar structural objects 11 and a grove of the pillar structural objects 11 which have uniform heights, are extended on a substrate 20, on which a working electrode 21 is formed, in the direction perpendicular to an electrode surface 21a of the working electrode 21 and stand at intervals of less than 100 μm. In FIG. 6, the dashed line indicates the profile surface at the distance $h_1$ in the direction perpendicular. Reference numeral 30 indicates a biological sample.

By placing the biological sample 30 above the working electrode 21 by pipetting operation under the microscope or using a guide in such a way that the horizontal distance between the working electrode 21 and the biological sample 30 (the distance in the direction parallel to the electrode surface 21a) is 0, the vertical distance z between the working electrode 21 and the lower end of the biological sample 30 can be controlled so as to fall within the range expressed by equation (4) without performing any other special operation. As a result, a diffusion path through which the dissolved substance in the solution is supplied is formed between the biological sample 30 and the working electrode 21. Therefore, the amount of a chemical substance to be detected generated from the biological sample 30 increases. Further, since the volume of space between the biological sample 30 and the working electrode 21 increases, the amount of part of the generated chemical substance that remains in this space increases. The two effects contribute to increase of the amount of the chemical substance that reaches the working electrode 21.

On the other hand, the amount of the chemical substance that scatters away without reaching the working electrode 21 may increase because the spacer 10 increases the diffusion distance between the biological sample 30 and the working electrode 21. However, since the distance $h_1$ is controlled by the spacer 10 so as to fall within an appropriate range, the two effects described above dominate and, as a result, the amount of the chemical substance that reaches the working electrode 21 may increase.

While the advantageous effects of the use of the spacer having uniform height in a plane has been described above, the height of a spacer do not need to be uniform in the entire region over the plane in which the electrode surface is positioned and a spacer may have a higher region and a lower region or may have a region in which the height gradually changes.

For example, a spacer may have an inverse cone structure in which a portion of the spacer positioned in the center of the electrode surface is lowest and in which a height of the spacer becomes higher as being away from the center of the electrode surface in an outer circumferential direction. By introducing a biological sample such as cells, which has a higher specific gravity than the solution, onto the working electrode equipped with the spacer by using a pipette or the like, the biological sample can be sunk by its own weight to the lowest position of the spacer, i.e. the center of the electrode surface without using any mechanism. In this way, not only the vertical distance but also the horizontal distance can be controlled with regard to the positional relationship of the biological sample with the electrode surface.

Further, by appropriately setting the relationship between the horizontal distance m from a point on the plane, in which the electrode surface is located, to the center of the electrode surface (the distance in a direction parallel to the electrode surface) and the height of the spacer at the point, z can be controlled so as to fall within a range of effective z determined in the simulation described above regardless of the sample diameter $d_{sp}$ as long as the sample diameter value is in the range of 100-600 μm.

Figure 7:
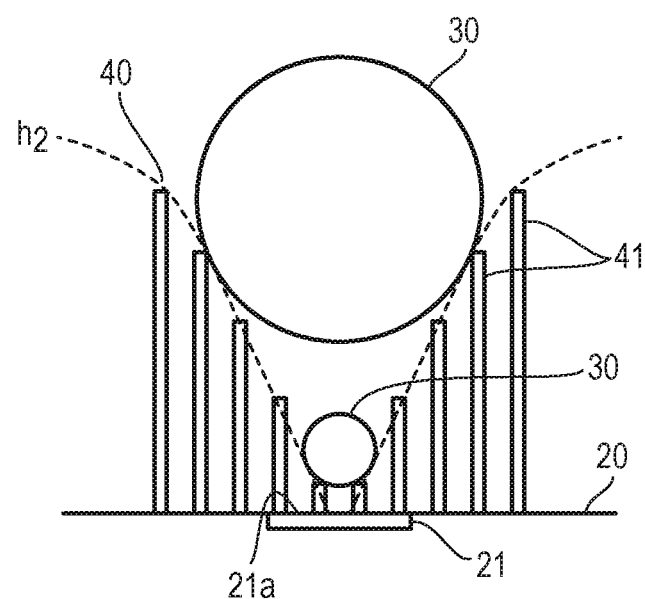
FIG. 7 is a schematic diagram for explaining an example configuration and arrangement of an inverse-cone-shaped spacer.

FIG. 7 illustrates an example of a spacer 40 that has such an inverse-cone-shaped structure. In FIG. 7, the spacer 40 having the inverse-cone-shaped structure is formed by a group of pillar structural objects 41 with gradually varying heights. A grove of the pillar structural objects 41 are extended on a substrate 20 on which a working electrode 21 is formed in the direction perpendicular to an electrode surface 21a of the working electrode 21 and stand at intervals of less than 100 μm.

Two biological samples 30 with two different diameter values $d_{sp}$ are illustrated in FIG. 7. Several values in the range of 100-600 μm given above are selected as the values of $d_{sp}$ as appropriate and a curve circumscribing an outline of all of the biological samples each of which is positioned at the height equal to the median of z expressed by equation (4) that corresponds to each of the values of $d_{sp}$, that is, $h_2$ indicated by the dashed line in FIG. 7, is fitted, thereby yielding approximately the following median expressed by equation (5) given below.

$$h_2 = \sqrt{\{(1.05d_{el}+6.89)m\} - 0.48d_{el} - 2.38 \pm 5 [\mu m]} \tag{5}$$

Specifically, a spacer that has a profile surface having an inverse-cone shape in which a distance $h_2$ in the direction vertical to the electrode surface satisfies equation (5) in response to the distance m in the direction parallel to the electrode surface from the center of the electrode surface of the working electrode, prevents the biological samples from entering a region on the electrode surface side of the profile surface, and allows a dissolved substance in a solution to diffuse may be placed in the solution, the biological samples may be positioned above the center of the electrode surface along the profile surface of the spacer and, in this state, electrochemical measurement may be performed.

When the biological samples 30 are placed, the biological sample 30 can be sunk to the concave portion of the inverse-cone-shaped spacer 40 by its own weight without needing special operation. At this point, the distance m between the working electrode 21 and the biological sample 30 in the direction parallel to the electrode surface 21a is 0. Note that since the position in which the biological sample 30 contacts the spacer 40 varies depending on the sample diameter $d_{sp}$, the distance z between the working electrode 21 and the lower end of the biological samples 30 varies depending on $d_{sp}$.

Like the configuration illustrated in FIG. 6, the configuration illustrated in FIG. 7 allows the amount of a chemical substance to be detected generated from the biological sample 30 to be increased because a diffusion path through which a dissolved substance in the solution is supplied is formed between the biological sample 30 and the working electrode 21. Further, since the volume of space between the biological sample 30 and the working electrode 21 increases, the amount of part of the generated chemical substance that remains in this space increases. The two effects contribute to increase of the amount of the chemical substance that reaches the working electrode 21.

On the other hand, the amount of the chemical substance that scatters away without reaching the working electrode 21 may increase because the spacer 40 increases the diffusion distance between the biological sample 30 and the working electrode 21. However, since the distance $h_2$ is controlled by the inverse-cone-shaped spacer 40 so as to fall in an appropriate range, the two effects described above dominate and, as a result, the amount of the chemical substance that reaches the working electrode 21 may increase.

While the spacers described above are formed by pillar structural objects, spacers are not so limited. For example, a porous structural object that has numerous holes with diameters less than 100 μm may be used as a spacer.

Specific Examples of Configurations Required in the Invention

The advantageous effects described above are expected to be achieved with any configurations of a biological sample, mechanism by which a chemical substance to be detected is generated or consumed in a biological sample, or a working electrode and a substance plate on which working electrodes are formed, as long as the condition that a chemical substance generated or consumed in a biological sample is electrochemically active or is transformed to another chemical substance that is electrochemically active is satisfied.

<Biological Samples>

While an embryoid body formed from mouse ES cells was chosen for the simulation, other samples such as cell aggregates, a single cell, pieces of tissue, microorganism or a non-biological sample containing a biologically-relevant substance may be used.

<Mechanism by which a Chemical Substance is Generated or Consumed in a Biological Sample>

While a generation mechanism that uses an ALP enzyme reaction on a sample was chosen for the simulation, generation or consumption by an enzyme reaction of other protein, peptide, RNA or the like or a catalytic reaction or other reaction with a platinum thin film or a titanium oxide film or the like on a sample may be used.

When a sample is cells or the like, the chemical substance may be a substance generated or consumed through various metabolic pathways or signaling pathways in cells. Examples include proton release in a metabolic pathway in a glycolytic system and dopamine release from nerve cells.

<Working Electrode>

While no specific material of the working electrode has been specified in the simulation, the working electrode may be made of any material that can be used as a working electrode for electrochemical measurement, such as a noble metal such as gold or platinum, an inorganic material predominantly composed of carbon such as graphite, diamond doped with an impurity, or carbon nanotubes, or a conductive polymer such as polypyrrole, polyaniline, or polythiophene.

The shape of the electrode surface of the working electrode is not limited to a circle and may be a shape such as an ellipse or polygon. In the case of a working electrode having a non-circular electrode surface, the diameter dimension $d_{el}$ specified in the present invention is the average of the lengths from the center of the shape to the whole edge of the shape.

<Working Electrode Formation Substrate>

While no specific material of the working electrode formation substrate was specified in the simulation, any material that can be used as a material of a working electrode support for electrochemical measurement, such as quartz, glass, silicon, or other ceramics may be used.

Examples of a Method for Fabricating a Spacer

The spacer needs to be made by a method that can control the height at micrometer level in order to achieve high effects of the present invention. Further, the spacer needs to allow a solution to pass through it, that is, needs to allow a dissolved substance in a solution to diffuse and also needs to be an electrical insulator if the spacer is fabricated on an electrode contiguously. As long as these conditions are satisfied, the spacer can achieve the intended effects regardless of a fabrication method and material of the spacer. Example spacer fabrication methods and materials that may be preferable are given below.

<Fabrication of a Spacer Made up of Pillar Structural Objects Through Film Deposition→Protective Layer Patterning→Etching>

1) Deposit a silicon nitride film having a controlled and uniform thickness on a substrate by CVD 2) Pattern an etching protective layer on the silicon nitride film by photolithography 3) Etch the silicon nitride film in regions not covered with the protective layer by reactive ion etching to form pillar structural objects 4) Remove the protective layer The insulating film material (the material of the pillar structural objects) may be silicon oxide, titanium oxide as well as silicon nitride The film deposition method may be a vacuum deposition method such as sputtering or vapor deposition or spin-on glass as well as CVD.

The patterning method may be a method such as screen printing or ink jet printing as well as photolithography.

The etching method may be plasma etching, sputter etching, ion beam etching, or wet etching as well as reactive ion etching.

<Fabrication of a Spacer Made up of a Group of Pillar Structural Objects by Structural Object Patterning Using Photosensitive Resin>

1) Coat an LSI having a current sensing element with photosensitive resin by spin coating 2) Fabricate pillar structural objects by photolithography The photosensitive resin may be any insulating and photosensitive resin that is used in common photolithography and photosensitive resin that is required for achieving required resolution needs to be chosen. In order to provide chemical stability for the pillar structural objects, epoxy chemically-amplified photosensitive resin used as negative permanent resist may be preferable.

The coating method may be any method that can control film thickness on the order of micrometers. Spin coating and spray coating may be preferable because of film-thickness controllability but coating such as dip coating, screen coating or roll coating may be used.

<Fabrication of a Spacer Formed of a Porous Structural Object by Gel Coating>

1) Prepare and heat an agarose water-diluted solution to 80° C. or higher to change it to a sol.

2) Drop the agarose water solution onto a substrate heated to 80° C. and form a thin film by spin coating. Keep the temperature of the substrate constantly at 80° C.
3) Let the substrate cool naturally to room temperature to acquire a porous spacer made of agarose gel.

The sol dropped onto the substrate may be any sol that changes to a porous gel after spin coating and heating temperature needs to be chosen that is appropriate for the type of sol. Substances such as agarose, polyvinyl alcohol, and cellulose are preferable because of ease of preparation and biocompatibility.

The coating method may be any method that has a mechanism that can control film thickness on the order of micrometers and keeps the temperature of the sol constant during the coating operation. Spin coating and spray coating may be preferable because of film-thickness controllability but dip coating, screen coating, roll coating or the like may be used.

<Other Conditions>

A spacer made up of pillar structural objects may be fabricated by other methods such as nanoimprint, molding such as mold-in, printing such as screen printing and ink-jet printing, or machining. A spacer made of a porous structural object may be acquired by placing a pre-shaped porous material such as porous silica or nitrocellulose membrane on a substrate.

Specifications for a Spacer Made Up of Pillar Structural Objects

Spacings and shape of a group of pillar structural objects used as a spacer need to be determined as follows.

<Spacings>

While spacings are less than 100 μm, the wider the spacings between pillar structural objects, the better, in terms of minimizing inhibition of diffusion of a dissolved substance around a biological sample by the pillar structural objects in order to achieve higher sensitivity.

Spacings between pillar structural objects do not need to be uniform and there may be a region in which pillar structural objects are densely located and a region in which pillar structural objects are sparsely located or a region in which no pillar structural object is located.

For example, a structure in which no pillar structural object is formed in a region immediately above the electrode surface and accordingly a biological sample is held only by pillar structural objects around the electrode surface can effectively prevent inhibition of diffusion of a dissolved substance immediately below the biological sample and can achieve higher sensitivity.

<Diameter>

There are no restrictions on the diameter of pillar structural objects as long as the strength that can hold a biological sample apart from an electrode surface can be provided. However, the smaller the diameter of pillar structural objects, the better, in order to minimize inhibition of diffusion of a dissolved substance around the sample by the pillar structural objects to achieve higher sensitivity.

<Top Surface Shape>

There are no restrictions on the shape of the top surface of a pillar structural object. Advantageous effects of the present invention can be achieved regardless of whether the top surface has a circular, triangular, rectangular or other polygonal shape.

A pillar structural object does not need to be a pillar structure that has the top and bottom surfaces that have identical shapes and areas. For example, the area of the top surface may be intentionally reduced or the top may be pointed for example by changing etching conditions for an insulating layer during fabrication.

If a biological sample is cells, a piece of tissue or the like, a contact area and adhesivity between the biological sample and pillar structural objects can be reduced by pointing the pillar structural objects. This effect is helpful for reducing the force required for pulling off the biological sample during removal of the biological sample after measurement on the biological sample and accordingly reducing damage to the biological sample.

Figure 8A:
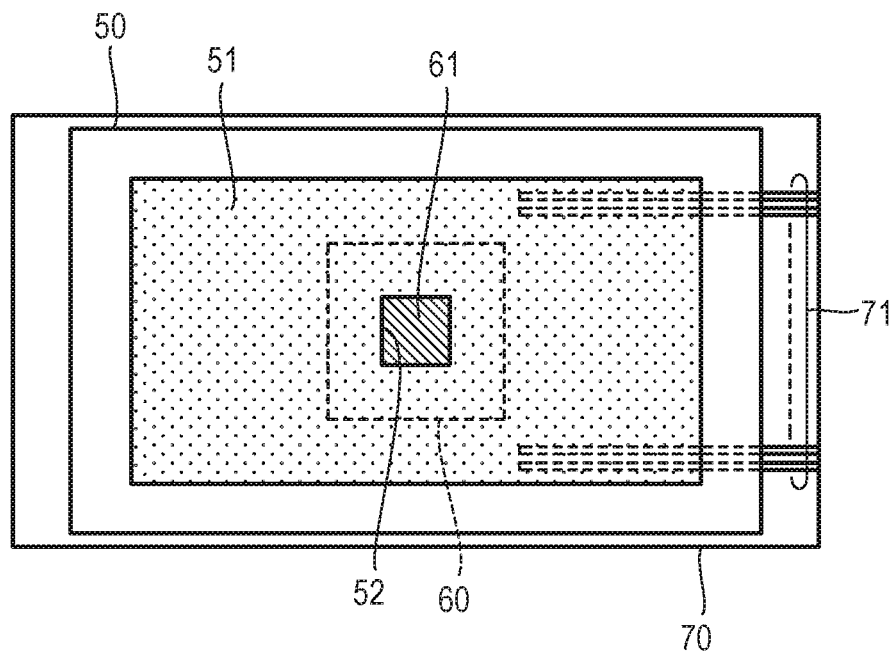
FIG. 8A is a plan view illustrating one example of a transducer according to the present invention and FIG. 8B is a cross-sectional view of the transducer illustrated in FIG. 8A.
Figure 8B:
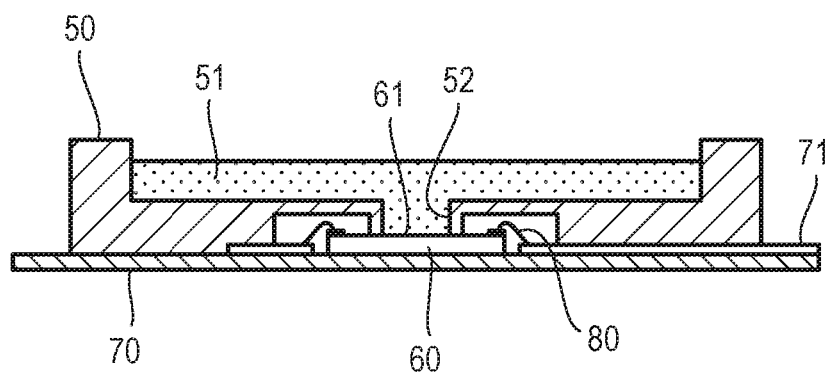
Figure 9:
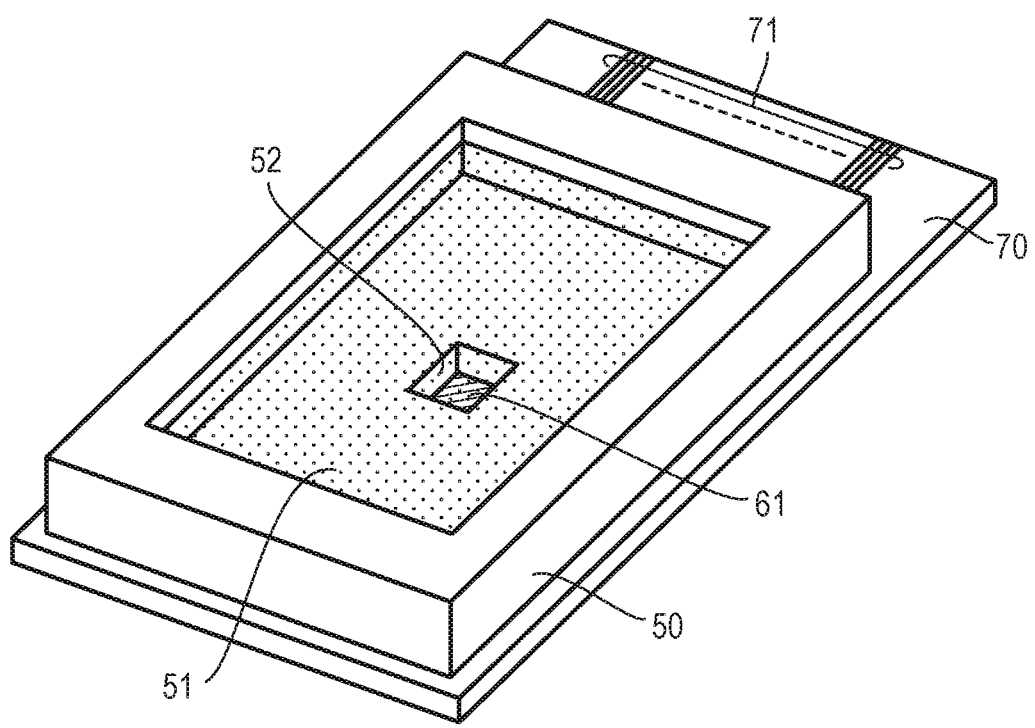
FIG. 9 is a perspective view of the transducer illustrated in FIG. 8A.

A specific configuration of a transducer according to the present invention used for electrochemical measurement of a chemical substance generated or consumed in a biological sample will be described with reference to FIGS. 8A, 8B and 9.

The transducer has a configuration in which an electrolytic solution well 50 that can contain a solution 51 and a biological sample immersed in the solution 51 is mounted on an LSI chip 60. A hole 52 is formed in the center of the electrolytic solution well 50 and the LSI chip 60 is disposed on the bottom end of the hole 52 in such a way that the LSI chip 60 covers the hole 52.

The LSI chip 60 and the electrolytic solution well 50 are mounted and fixed on a substrate 70 and a pattern 71 of many conductors for connection with an external device that controls the transducer is formed on the substrate 70. Reference numeral 80 in FIG. 8B indicates bonding wires that interconnect the LSI chip 60 and the pattern 71 of conductors.

A sensor region 61 is formed on the top surface of the LSI chip 60. In FIG. 8A, the sensor region 61 is indicated by hatching and is defined in the position of the hole 52 in the bottom surface of the electrolytic solution well 50. While details are omitted from the figure, electrodes (working electrodes) are formed in the sensor region 61 and spacers made of pillar structural objects as described above are fabricated above the working electrodes. The LSI chip 60 includes the functions such as the function of applying a voltage to the working electrodes, the function of detecting a reaction at the working electrode as a current value, and the function of amplifying the current value.

Note that a group of pillar structural objects making up a spacer may have uniform heights or may have a profile surface having an inverse-cone shape. Further, a spacer may be formed of a porous structure instead of pillar structural objects.

What is claimed is:

1. A method for electrochemically detecting a chemical substance generated or consumed in a biological sample immersed in a solution, the method comprising:
    performing a simulation including:
    a) setting following parameters beforehand and keeping the following parameters constant during the simulation,
        i) a dimension of an electrode surface of a working electrode for undergoing an oxidation-reduction reaction with the chemical substance, and
        ii) a dimension of the biological sample;
    b) obtaining a relation between a current flowing through the working electrode and a vertical distance, the vertical distance being a distance between the biological sample and the electrode surface in a direction perpendicular to the electrode surface, the current being calculated based on i) a chemical reaction rate at which the biological sample generates or consumes the chemical substance, ii) a change in a concentration distribution of the chemical substance in the solution, and iii) a rate at which electrons are supplied and received to and from the chemical substance at the electrode surface, and c) determining a range of the vertical distance, within the range the current taking a maximum value and being greater than or equal to 90% of the maximum value; and detecting electrochemically, after the performing of the simulation, the chemical substance with the biological sample placed in the solution at a distance away from the electrode surface in the vertical direction, the distance being within the range, the electrode surface having the dimension set in the simulation, the biological sample having the dimension set in the simulation.

2. A method for electrochemically detecting a chemical substance generated or consumed in a biological sample immersed in a solution, the method comprising:

placing the biological sample on a spacer secured in the solution, the biological sample having a diameter dimension between 100 μm, inclusive, and 600 μm, inclusive, the spacer having a profile surface to keep the biological sample away from an electrode surface of a working electrode, the working electrode being configured to undergo an oxidation-reduction reaction with the chemical substance, the profile surface being situated away from the electrode surface in a direction perpendicular to the electrode surface by a constant height $h_1$, the constant height $h_1$ being within a range from $$21.8 \frac{d_{el}+0.8}{d_{el}+9.7} - 5 \ [\mu m] \ to$$

$$21.8 \frac{d_{el}+0.8}{d_{el}+9.7} + 5 \ [\mu m],$$

$d_{el}$ representing a diameter dimension of the electrode surface and being less than or equal to 80 μm, the spacer being configured to allow a dissolved substance to diffuse in the solution; and detecting electrochemically the chemical substance with use of the working electrode.

3. A method for electrochemically detecting a chemical substance generated or consumed in a biological sample immersed in a solution, the method comprising:

placing the biological sample on a spacer secured in the solution to put the biological sample immediately above a center of an electrode surface of a working electrode, the working electrode being configured to undergo an oxidation-reduction reaction with the chemical substance, the biological sample having a diameter dimension between 100 μm, inclusive, and 600 μm, inclusive, the spacer having an inverse-cone-shaped profile surface to keep the biological sample away from the electrode surface, the profile surface being situated away from the electrode surface in a direction perpendicular to the electrode surface by a height $h_2$, the height $h_2$ at a position away from the center of the electrode surface in a direction parallel to the electrode surface by m [μm] being within a range from $$\sqrt{(1.05 \ d_{el}+6.89)m} - 0.48 \ d_{el} - 2.38 - 5 \ [\mu m] \ to$$

-continued
$$\sqrt{(1.05 \ d_{el}+6.89)m} - 0.48 \ d_{el} - 2.38 + 5 \ [\mu m],$$

$d_{el}$ representing a diameter dimension of the electrode surface and being less than or equal to 80 μm, the spacer being configured to allow a dissolved substance in the solution to diffuse; and detecting electrochemically the chemical substance via the working electrode.

4. A device for electrochemically detecting a chemical substance generated or consumed in a biological sample immersed in a solution, the device comprising:

a solution well configured to accommodate the solution;

a working electrode configured to undergo an oxidation-reduction reaction with the chemical substance, the working electrode having an electrode surface with a diameter dimension $d_{el}$ less than or equal to 80 μm; and a spacer provided in the solution well, the spacer having a profile surface configured to keep the biological sample away from the electrode surface of the working electrode, the profile surface being situated away from the electrode surface in a direction perpendicular to the electrode surface by a constant height $h_1$, the constant height $h_1$ being within a range from $$21.8 \frac{d_{el}+0.8}{d_{el}+9.7} - 5 \ [\mu m] \ to$$

$$21.8 \frac{d_{el}+0.8}{d_{el}+9.7} + 5 \ [\mu m],$$

the spacer being configured to allow a dissolved substance to diffuse in the solution.

5. The device according to claim 4, wherein the spacer is made up of pillar structural objects, each of which being extended in the direction perpendicular to the electrode surface and standing at intervals of less than 100 μm.

6. The device according to claim 4, wherein the spacer is formed of a porous structure having pores with a diameter of less than 100 μm.

7. A device for electrochemically detecting a chemical substance generated or consumed in a biological sample immersed in a solution, the device comprising:

a solution well configured to accommodate the solution;

a working electrode configured to undergo an oxidation-reduction reaction with the chemical substance, the working electrode having an electrode surface with a diameter dimension $d_{el}$ less than or equal to 80 μm; and a spacer provided in the solution well, the spacer having an inverse-cone-shaped profile surface to keep the biological sample away from the electrode surface of the working electrode, the profile surface being situated away from the electrode surface in a direction perpendicular to the electrode surface by a height $h_2$, the height $h_2$ at a position away from a center of the electrode surface in a direction parallel to the electrode surface by m [μm] being within a range from $$\sqrt{(1.05 \ d_{el}+6.89)m} - 0.48 \ d_{el} - 2.38 - 5 \ [\mu m] \ to$$

$$\sqrt{(1.05 \ d_{el}+6.89)m} - 0.48 \ d_{el} - 2.38 + 5 \ [\mu m],$$

the spacer being configured to allow a dissolved substance to diffuse in the solution.

8. The device according to claim 7, wherein the spacer is made up of pillar structural objects, each of which being extended in the direction perpendicular to the electrode surface and standing at intervals of less than 100 µm.

9. The device according to claim 7, wherein the spacer is formed of a porous structure having pores with a diameter of less than 100 µm.

10. A transducer for electrochemically detecting a chemical substance generated or consumed in a biological sample immersed in a solution, the transducer comprising:
a large-scale integrated chip;
a solution well configured to accommodate the solution, the solution well having a bottom thereof closed by the large-scale integrated chip;
an electrode on the large-scale integrated chip, the electrode having an electrode surface with a diameter dimension $d_{el}$ less than 80 µm; and
a spacer having a profile surface to keep the biological sample away from the electrode surface of the electrode, the profile surface being situated away from the electrode surface in a direction perpendicular to the electrode surface by a constant height $h_1$, the constant height $h_1$ being within a range from $$21.8 \frac{d_{el} + 0.8}{d_{el} + 9.7} - 5 \; [\mu m] \; \text{to}$$

$$21.8 \frac{d_{el} + 0.8}{d_{el} + 9.7} + 5 \; [\mu m],$$

the spacer being configured to allow a dissolved substance to diffuse in the solution.

11. The transducer according to claim 10, wherein the spacer is made up of pillar structural objects, each of which being extended in the direction perpendicular to the electrode surface and standing at intervals of less than 100 µm.

12. The transducer according to claim 10, wherein the spacer is formed of a porous structure having pores with a diameter of less than 100 µm.

13. A transducer for electrochemically detecting a chemical substance generated or consumed in a biological sample immersed in a solution, the transducer comprising:
a large-scale integrated chip;
a solution well accommodating the solution, the solution well having a bottom thereof closed by the large-scale integrated chip;
an electrode on the large-scale integrated chip, the electrode having an electrode surface with a diameter dimension $d_{el}$ less than 80 µm; and
a spacer having an inverse-cone-shaped profile surface to keep the biological sample away from the electrode surface of the electrode, the profile surface being situated away from the electrode surface in a direction perpendicular to the electrode surface by a height $h_2$, the height $h_2$ at a position away from a center of the electrode surface in a direction parallel to the electrode surface by m [µm] being within a range from $$\sqrt{(1.05 \, d_{el} + 6.89)m} - 0.48 \, d_{el} - 2.38 - 5 \; [\mu m] \; \text{to}$$

$$\sqrt{(1.05 \, d_{el} + 6.89)m} - 0.48 \, d_{el} - 2.38 + 5 \; [\mu m],$$

the spacer being configured to allow a dissolved substance to diffuse in the solution.

14. The transducer according to claim 13, wherein the spacer is made up of pillar structural objects, each of which being extended in the direction perpendicular to the electrode surface and standing at intervals of less than 100 µm.

15. The transducer according to claim 13, wherein the spacer is formed of a porous structure having pores with a diameter of less than 100 µm.

* * * * *